United States Patent [19]

Yabe et al.

[11] Patent Number: 5,551,945

[45] Date of Patent: Sep. 3, 1996

[54] ENDOSCOPE SYSTEM INCLUDING ENDOSCOPE AND PROTECTION COVER

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamada, both of Hachioji, all of Japan

[73] Assignee: Olympus Optical Co., Ltd., Tokyo, Japan

[21] Appl. No.: 52,450

[22] Filed: Apr. 28, 1993

[30] Foreign Application Priority Data

| Mar. 16, 1993 | [JP] | Japan | 5-011594 U |
| Mar. 16, 1993 | [JP] | Japan | 5-011597 U |
| Mar. 16, 1993 | [JP] | Japan | 5-055860 U |

[51] Int. Cl.⁶ ........................ A61B 1/00
[52] U.S. Cl. ............. 600/122; 600/121; 600/131; 600/146
[58] Field of Search ............ 128/4, 6; 600/121, 600/122, 131, 146

[56] References Cited

U.S. PATENT DOCUMENTS

| 3,035,691 | 5/1962 | Rasmussen et al. . |
| 3,633,758 | 1/1972 | Morse . |
| 4,366,901 | 1/1983 | Short . |
| 4,404,963 | 9/1983 | Kohri ........................... 128/4 |
| 4,646,722 | 3/1987 | Silverstein et al. . |
| 4,715,360 | 12/1987 | Akui et al. . |
| 4,721,097 | 1/1988 | D'Amelio . |
| 4,741,326 | 5/1988 | Sidall et al. . |
| 4,779,727 | 10/1988 | Taterka et al. . |
| 4,825,850 | 5/1989 | Opie et al. . |
| 4,858,001 | 8/1989 | Milbank et al. . |
| 4,869,238 | 9/1989 | Opie et al. . |
| 4,877,033 | 10/1989 | Seitz . |
| 4,878,485 | 11/1989 | Adair . |
| 4,947,827 | 8/1990 | Opie et al. . |
| 4,991,564 | 2/1991 | Takahashi et al. . |
| 4,991,565 | 2/1991 | Takahashi et al. . |
| 5,025,778 | 6/1991 | Silverstein et al. . |
| 5,042,112 | 8/1991 | Dunklee . |
| 5,050,585 | 9/1991 | Takahashi . |
| 5,105,942 | 4/1992 | van Veen et al. . |
| 5,131,537 | 7/1992 | Gonzales . |
| 5,198,894 | 3/1993 | Hicks . |
| 5,201,908 | 4/1993 | Jones . |
| 5,217,001 | 6/1993 | Nakao et al. . |
| 5,237,984 | 8/1993 | Williams, III et al. . |
| 5,257,617 | 11/1993 | Takahashi ........................... 128/4 |
| 5,301,657 | 4/1994 | Lafferty et al. . |
| 5,419,311 | 5/1995 | Yabe et al. ........................... 128/4 |

FOREIGN PATENT DOCUMENTS

| 0341719A1 | 11/1989 | European Pat. Off. . |
| 0349479A1 | 1/1990 | European Pat. Off. . |
| 4325138 | 11/1992 | Japan . |

*Primary Examiner*—Richard J. Apley
*Assistant Examiner*—Beverly M. Flanagan
*Attorney, Agent, or Firm*—Watson Cole Stevens Davis, P.L.L.C.

[57] ABSTRACT

In an endoscope system including an endoscope having an insertion section to be inserted into a cavity under inspection, a bending portion which is provided in said insertion section near a distal end thereof and is bendable in at least two different directions and an operation section to which a proximal end of the insertion section is connected and a disposable protection cover having an insertion section cover for covering said insertion section of the endoscope and having formed therein an insertion section inserting channel into which said insertion section of the endoscope is insertable and at least one conduit channel, said insertion section and bending portion of the endoscope are formed to have a non-circular lateral cross section, a direction in which said non-circular cross section has a larger size is aligned with a direction in which said bending portion is bent by a maximum bending angle or a direction in which said non-circular cross section has a smaller size is aligned with a direction in which said bending portion is bent by a minimum bending angle.

1 Claim, 16 Drawing Sheets

FIG_1
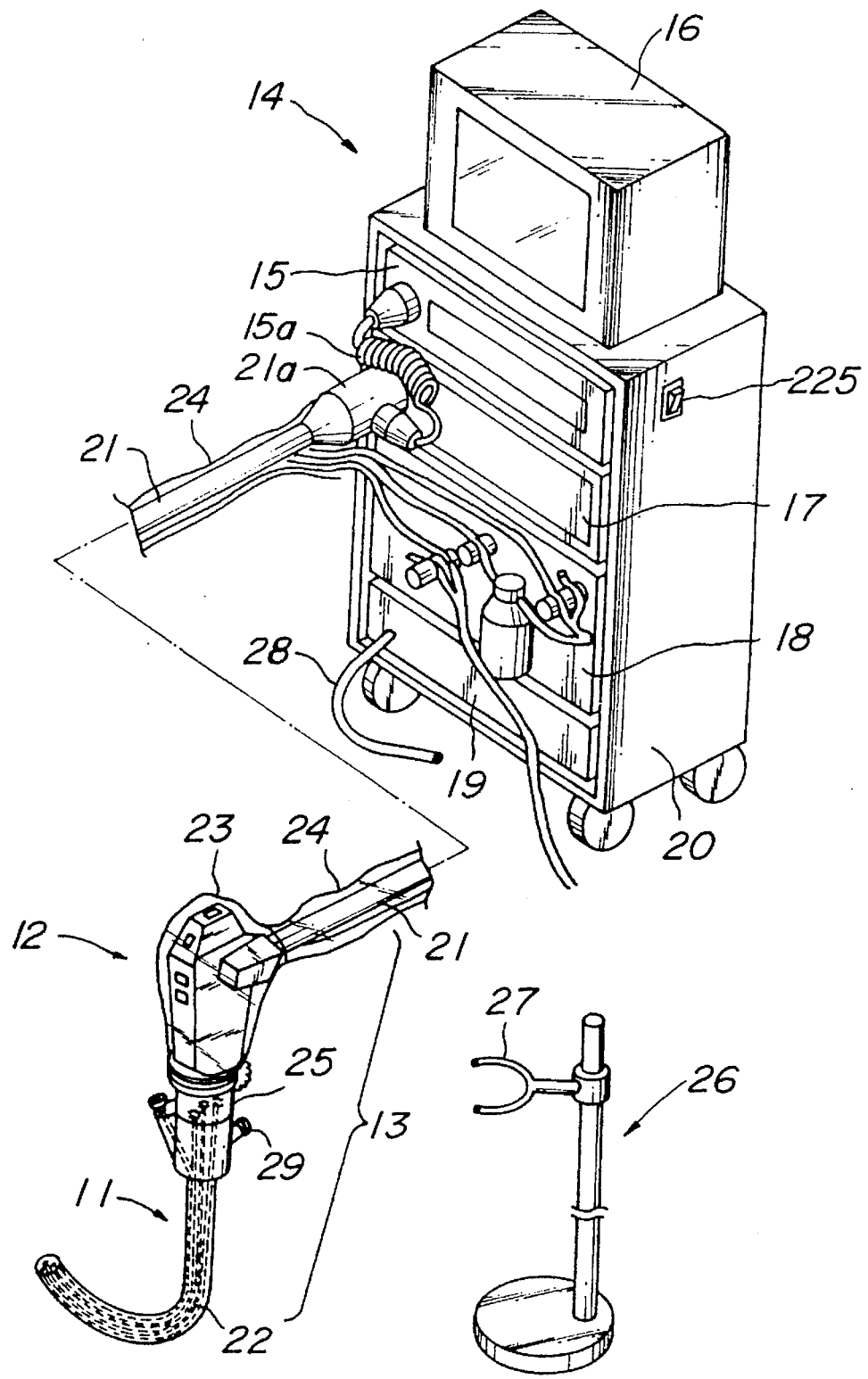

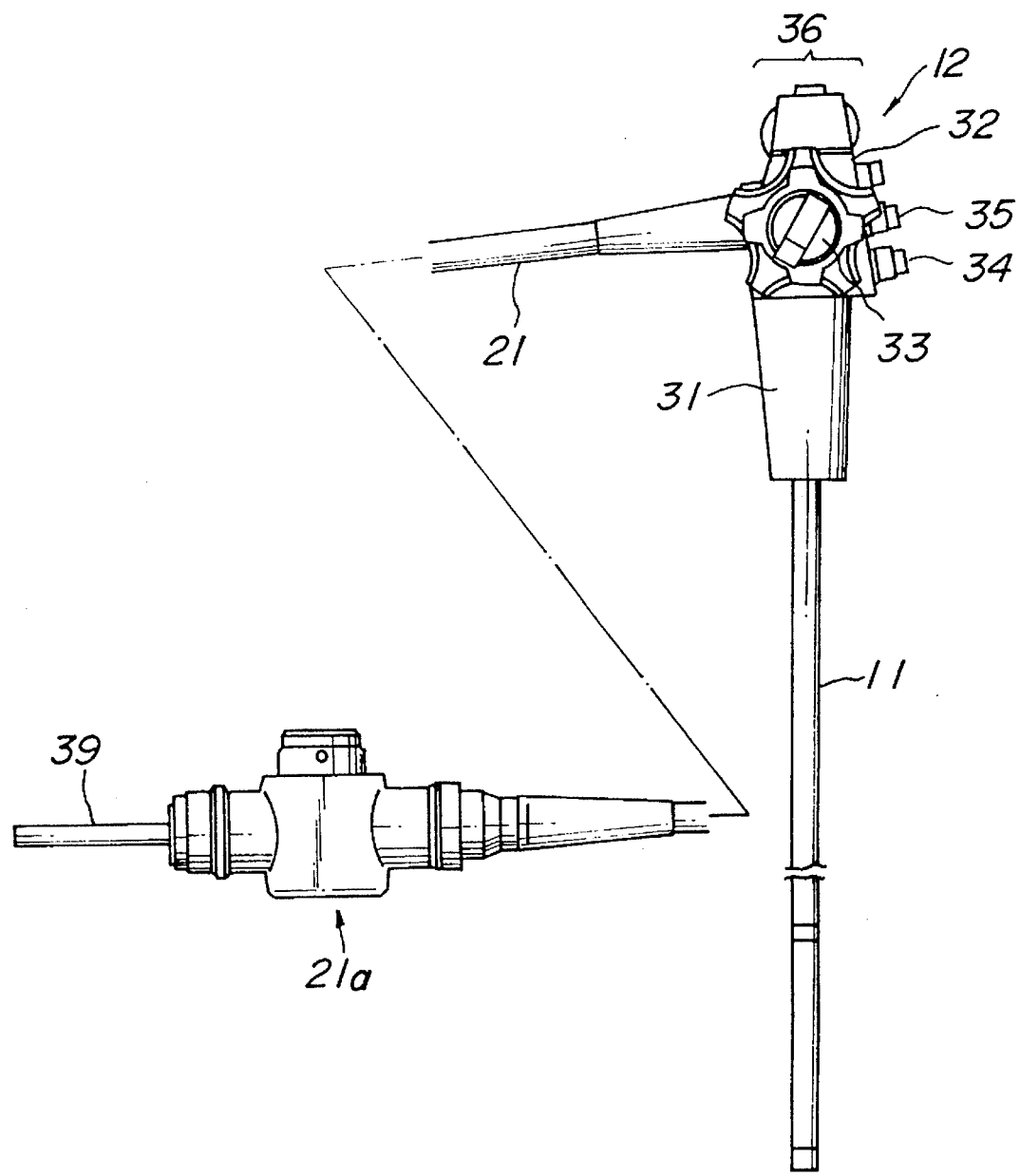
FIG._2

FIG_3
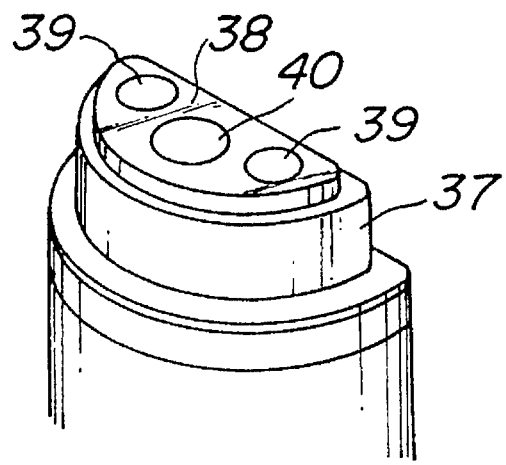
FIG_4
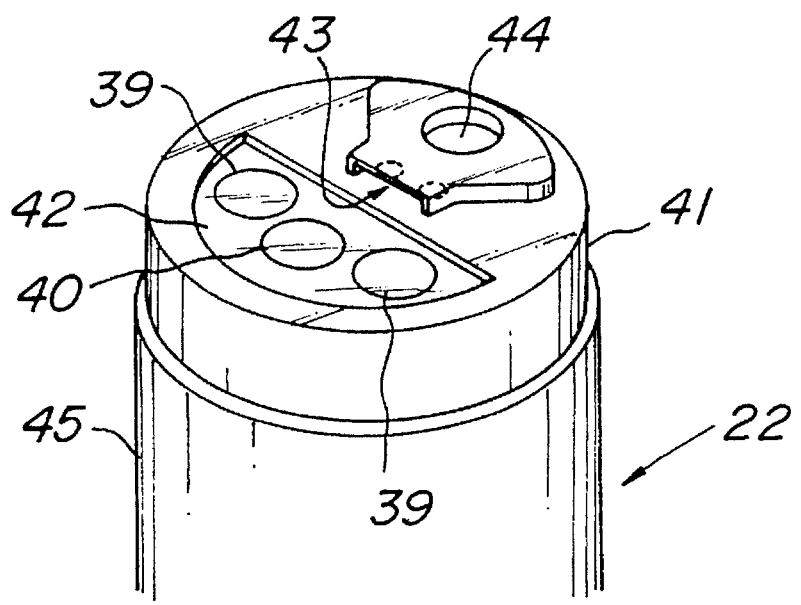

FIG_6
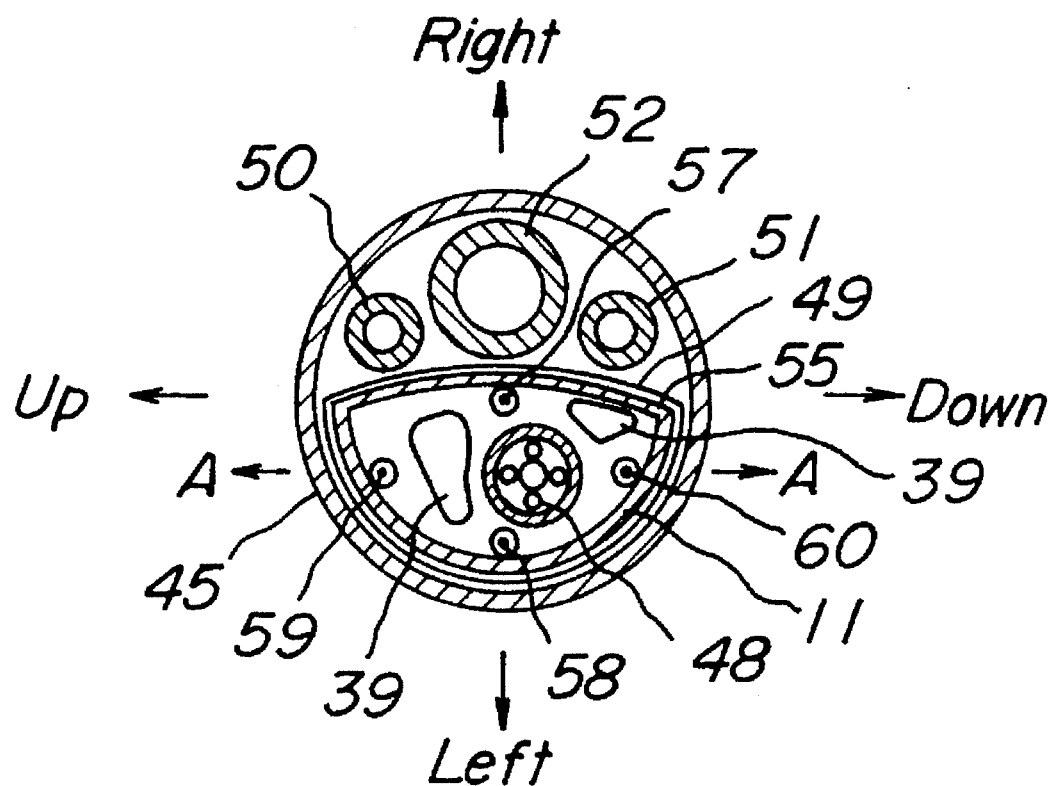

FIG_8
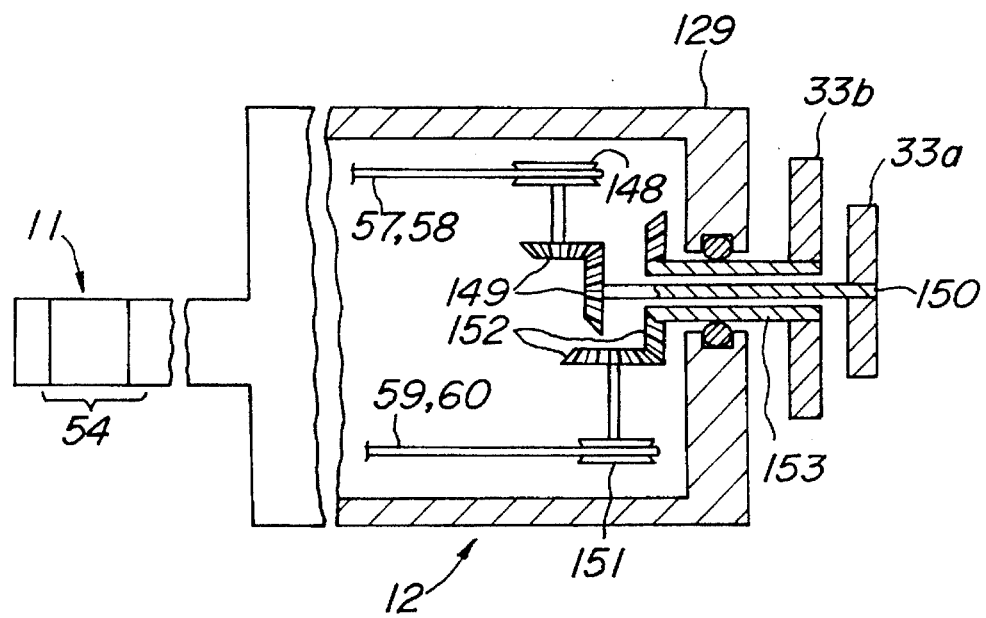
FIG_9
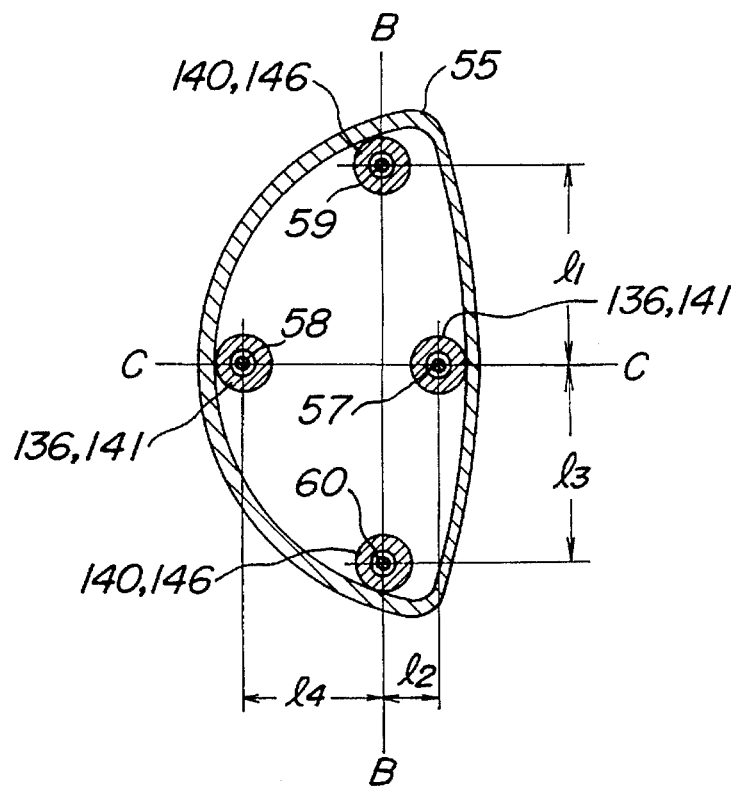

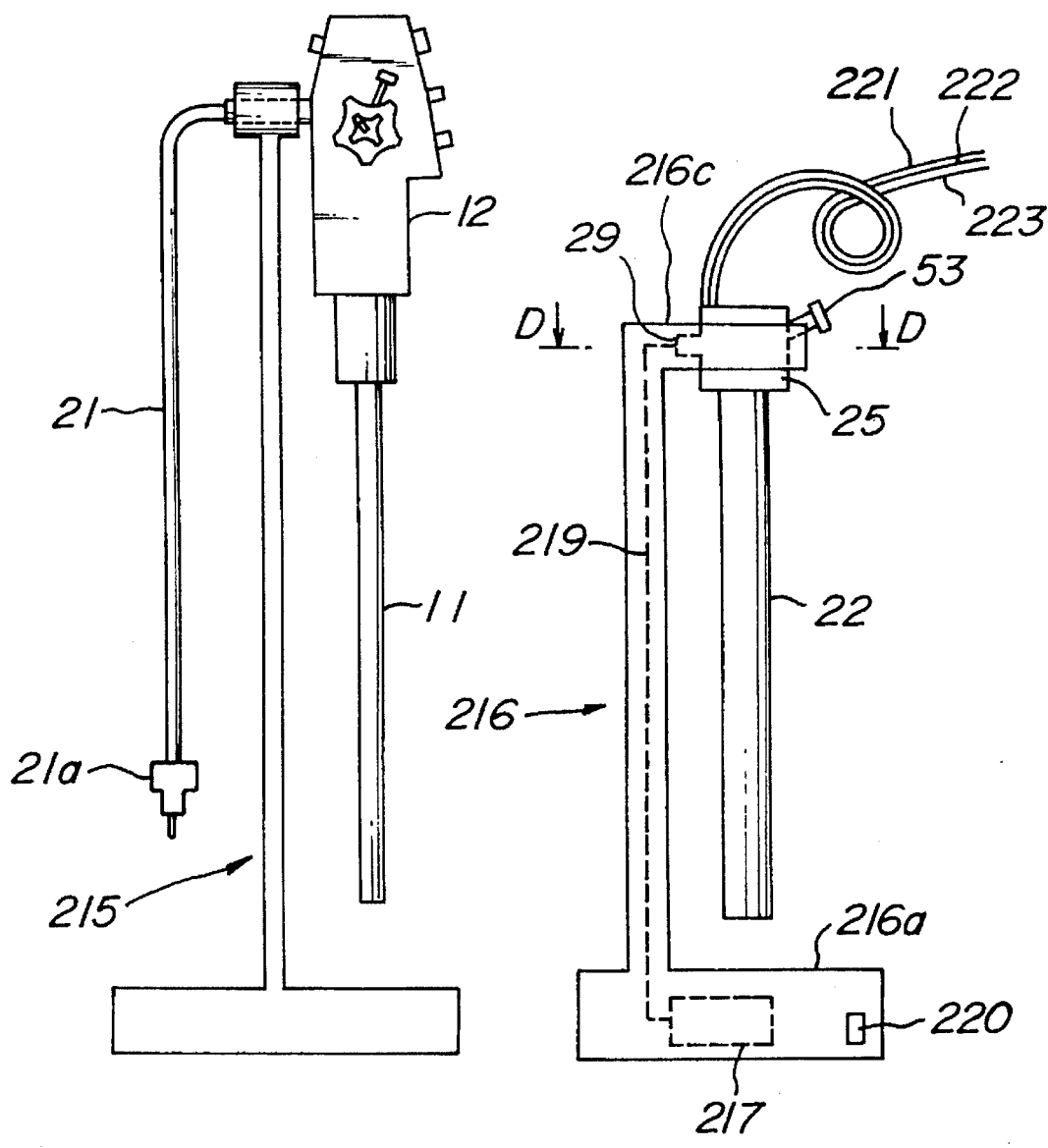

FIG_12
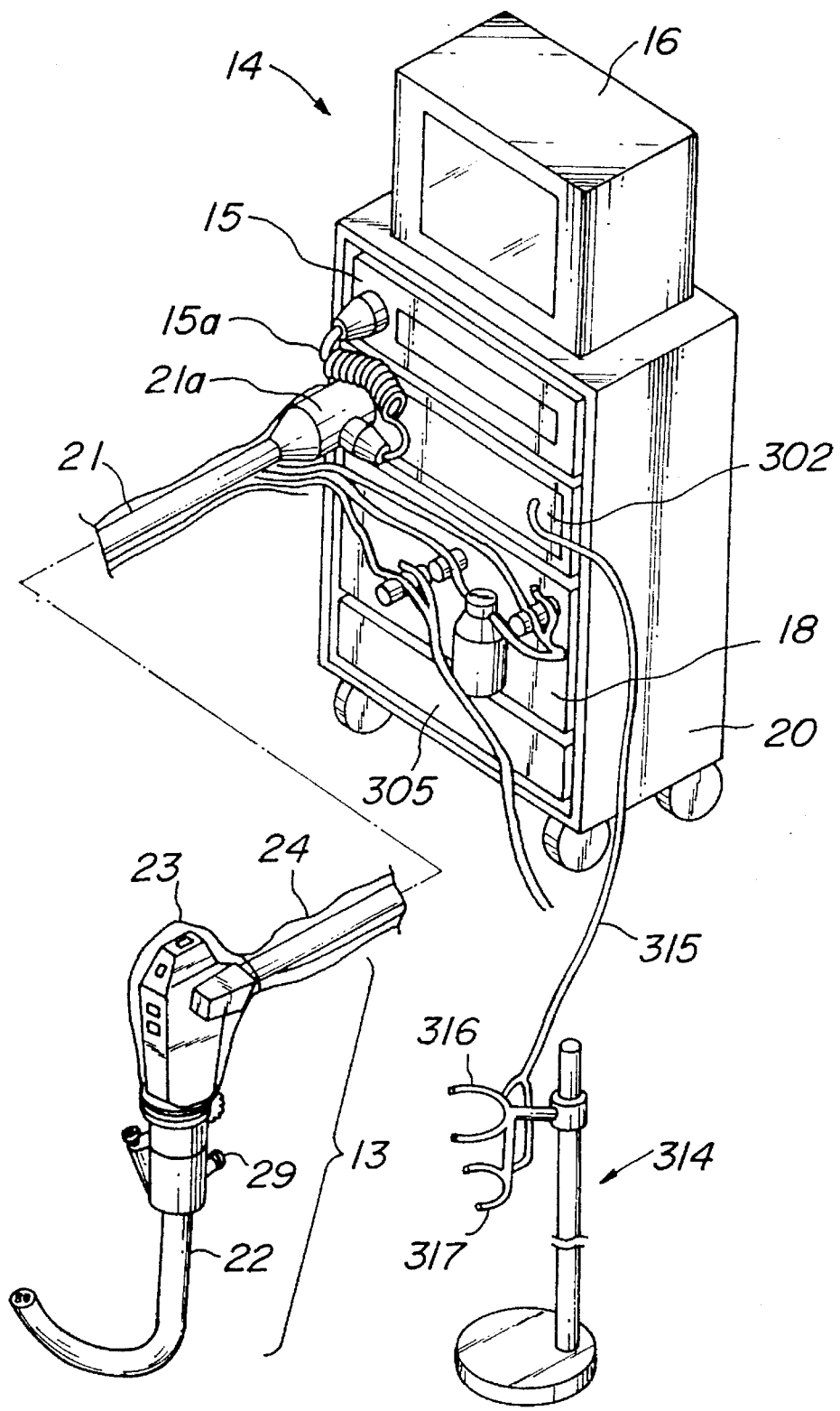

FIG_13
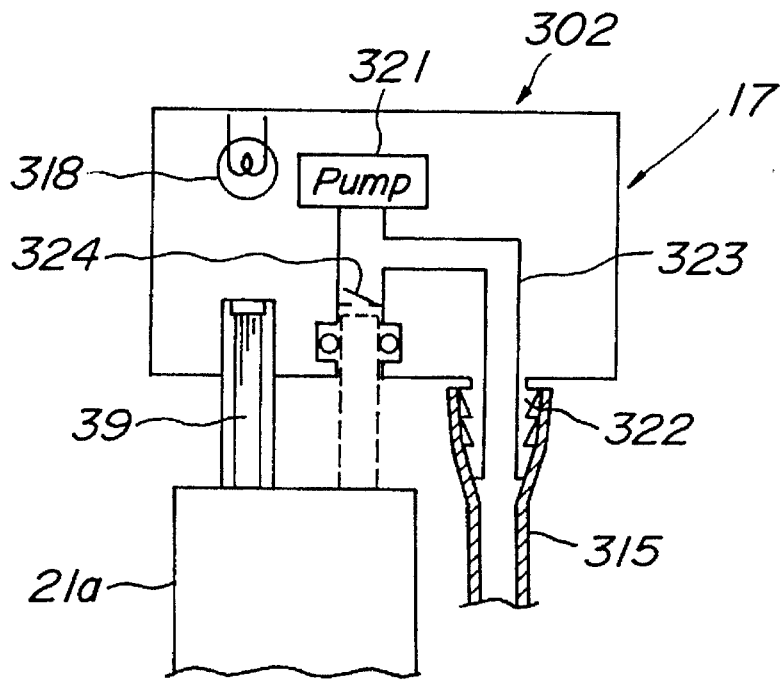
FIG_14
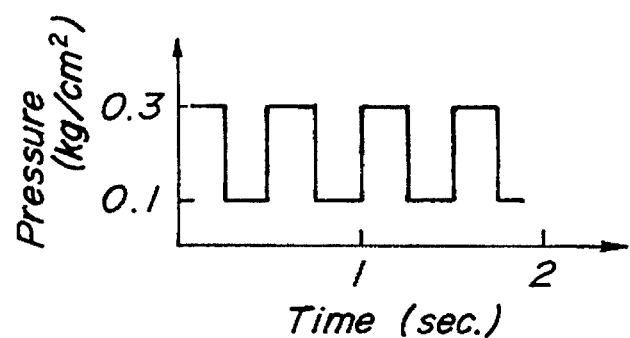

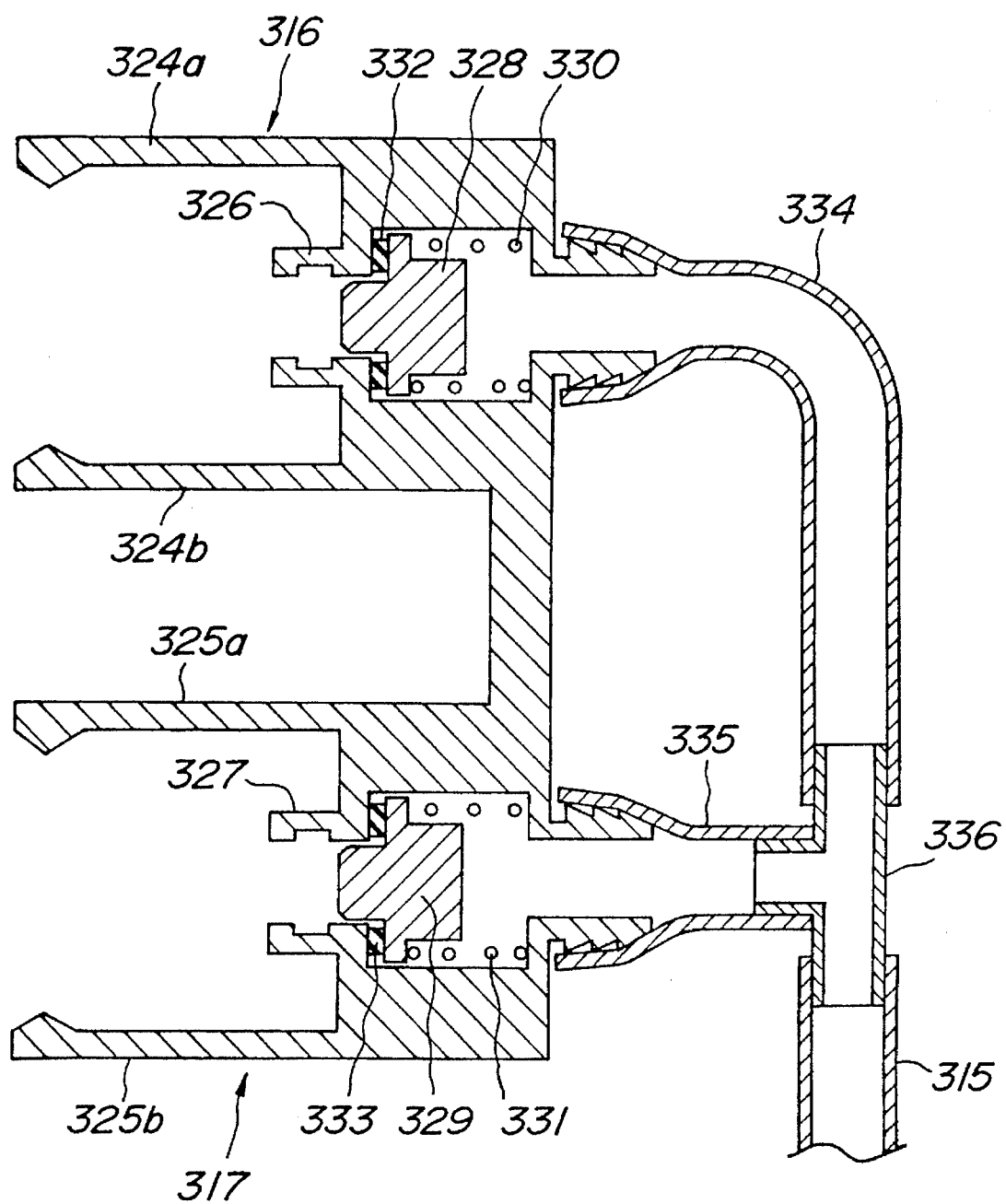
FIG_15

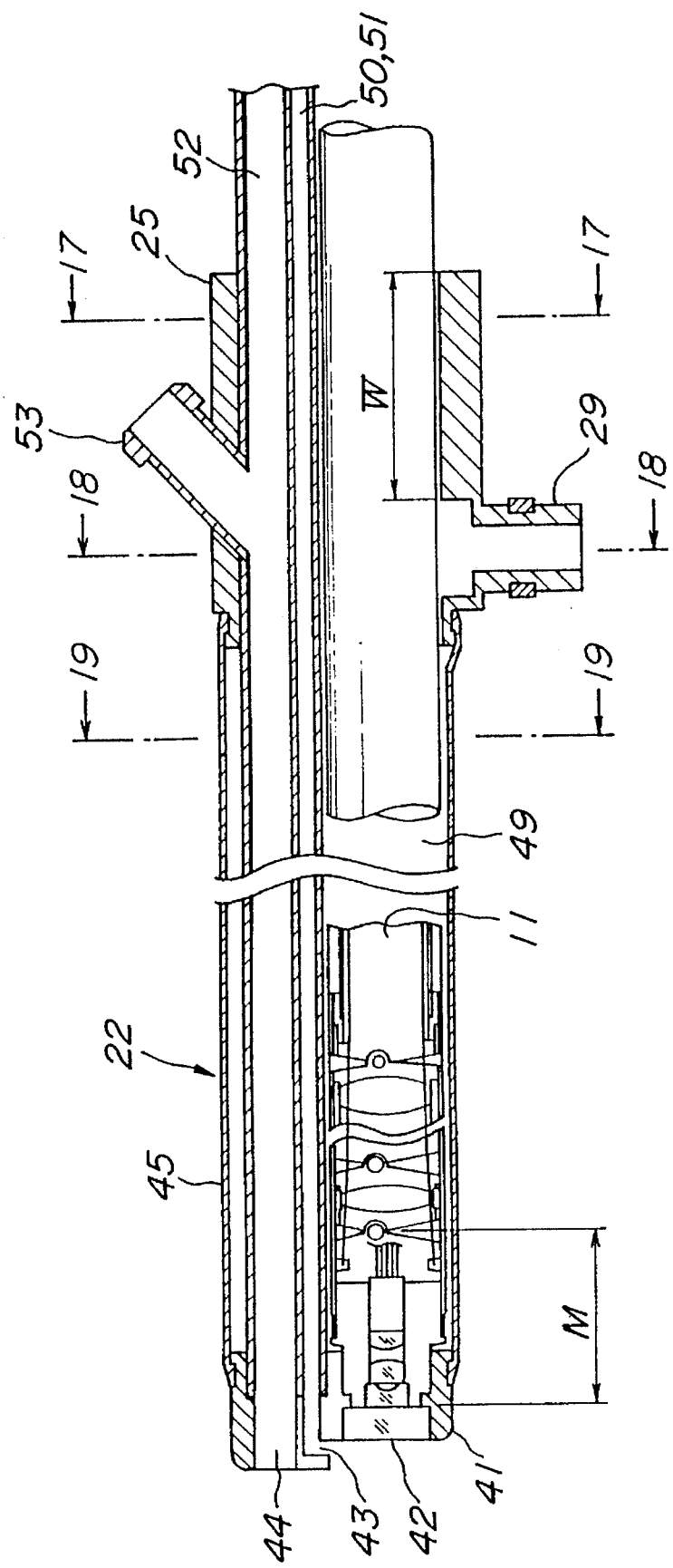

FIG_17
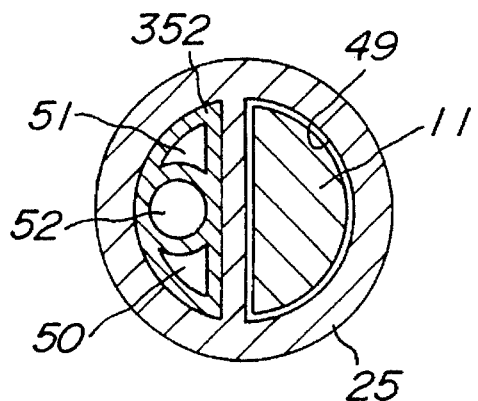
FIG_18
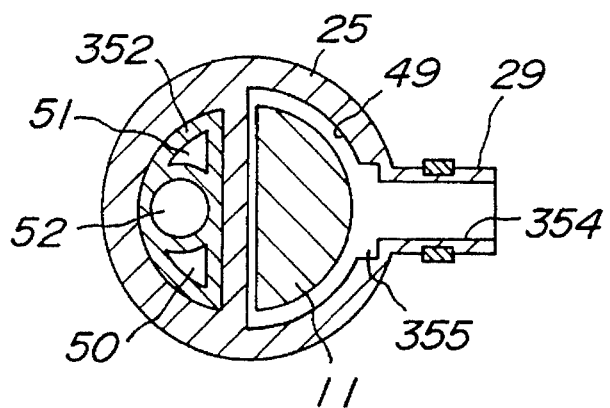
FIG_19
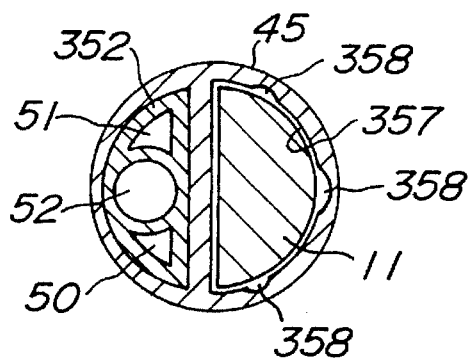

ENDOSCOPE SYSTEM INCLUDING ENDOSCOPE AND PROTECTION COVER

BACKGROUND OF THE INVENTION

1. Field of the Invention

The present invention relates to an endoscope system including an endoscope and a disposable protection cover for covering the endoscope, and also relates to a disposable protection cover, an endoscope and an apparatus for supporting the disposable protection cover for use in the endoscope system.

2. Description of the Related Art

An endoscope system has been widely utilized for providing diagnostic and therapeutic indications for coeliac cavities of patients and for inspecting an inside of a mechanical structure. To this end, there have been developed various kinds of endoscopes. For instance, in order to inspect or treat the esophagus stomach and duodenum, upper endoscopes have been utilized. Further, colonoscopes have been developed to examine colons and sigmoidoscopes have been proposed to inspect rectums and sigmoid colons. In case of using the endoscope, an insertion portion of the endoscope has to be inserted into a cavity of a patient, so that the outer surface of the insertion section of the endoscope is contaminated with living tissues and liquids. When the thus contaminated endoscope is successively used for another patient, there might be a possibility of infection. Therefore, once the endoscope is used to diagnose and/or treat a patient, it is necessary to clean and sterilize the endoscope. Of course, the cleaning of the endoscope requires a substantial time and during this cleaning time, it is impossible to perform the endoscopic procedure by using this endoscope. In order to mitigate such an idle time, it is necessary to prepare a large number of endoscopes. However, the endoscope is rather expensive, so that it is practically difficult to prepare a large number of endoscopes particularly in a small hospital or clinic. Therefore, in almost all hospitals and clinics, in practice, after the endoscope has been used for examining or treating a patient, the endoscope is immediately cleaned. Typically, this cleaning requires several minutes to ten minutes. In order to effect the complete washing and sterilization, the cleaning has be to performed for several tens of minutes.

Further, the endoscope has various channels such as air channel, water channel, suction channel, foceps channel which extend along the insertion section from a proximal end to a distal end thereof, and these channels except the foceps channel are connected via tubes to respective devices such as an air supply pump, water supply pump, water suction pump and air suction pump. These channels are subjected to contact with living tissues and liquids. However, in order to clean these channels of the endoscope completely, a relatively long time is required. Then, the endoscope could not be utilized efficiently for the long cleaning time. In a large hospital or clinic, a large number of endoscopes may be prepared in order to mitigate the problem of cleaning time. However, this solution results in the increase in the running cost. Further, in small clinics, it is practically impossible to prepare a number of expensive endoscopes.

Moreover, the endoscope might be broken during the cleaning and the usable time of the endoscope is liable to be shortened by the cleaning.

In order to avoid the above explained various problems, there has been proposed an endoscope system, in which the endoscope is covered with a disposable protection sheath-like cover having channels formed therein. For instance, U.S. Pat. Nos. 4,721,097, 4,741,3126, 4,825,850, 4,869,238, 4,991,564, 4,991,565, 5,050,585 disclose various kinds of disposable protection sheath-like covers having channels formed therein. In U.S. Pat. No. 4,646,722, there is shown an endoscope system in which the endoscope is covered with a protection sheath, while a tube having channels formed therein is inserted into the U-shaped cutout formed in an outer surface of the endoscope along a longitudinal axis thereof. Upon diagnosis, the insertion section of the endoscope is covered with the protection sheath, and after the inspection, the sheath is removed from the insertion section and is then discarded. Therefore, it is no more necessary to clean the endoscope after every inspection.

In the above mentioned U.S. Patents, the protection sheath-like cover is constructed to cover only the insertion section of the endoscope, but does not cover an operation section of the endoscope. It should be noted that the operation section of the endoscope is treated by hands of doctors and operators and thus is brought into contact with the living tissues and liquids of a patient. Therefore, in order to remove the contamination of the operation section of the endoscope due to such living tissues and liquids, it is advantageous to cover not only the insertion section, but also the operation section of the endoscope. In European Pat. Publication No, 0 349 479 Al, there is disclosed an endoscope system, in which not only the insertion section, but also the operation section of the endoscope are covered with a disposable protection cover. That is to say, the protection cover comprises a sheath-like portion for covering the insertion section of the endoscope and a bag-like portion for covering the operation section, said sheath-like portion and bag-like portion being integrally formed. It has been also proposed to form the sheath-like portion and bag-like portion as separate covers. For instance, in European Pat. Publication No. 0 341 719 Al, there is proposed another known endoscope system, in which an insertion section of an endoscope is covered with a disposable protection sheath-like cover and an operation section of the endoscope is covered with a disposable protection bag-like cover which is mated or Joined with the protection sheath-like cover in order to prevent the contamination through the junction of the sheath-like cover and the bag-like cover.

In order to treat a cavity of a patient body, there has been proposed to arrange a forceps channel within the sheath-like cover into which an endoscope is inserted.

As explained above, the disposable protection cover is inserted into a cavity of a patient, so that its lateral cross section should be circular. Further, in the protection cover, there are formed the forceps channel, air supply conduit channel and water supply conduit channel. These channels are extended within the protection cover. In a lateral cross section of the protection cover, these channels are arranged in a substantially semicircular space and the endoscope is inserted into the remaining substantially semicircular space, so that the insertion section of the endoscope should have a lateral cross section having a substantially semicircular shape. Moreover, in order to improve the examination, the distal end of the insertion section of the endoscope is bent in up and down directions as well as in right and left directions by operating angle knobs provided on the operation section of the endoscope. To this end a bending portion is provided near the distal end of the insertion section and a lateral cross section of this bending portion is also substantially semicircular. Then, a moment necessary for bending the distal end portion of the insertion section in some directions would be increased in relation to a width of the bending portion. That is to say, the bending portion could be easily bent in a direction which is substantially perpendicular to a diametric base side in the lateral cross section, but could not be easily bent in a direction which is substantially parallel with said diametric base side.

when the operation section of the endoscope is covered with the operation section cover, a shaft to which the angle knobs for bending the bending portion of the insertion section are secured has to be protruded from the operation section cover. Usually said shaft is provided on a side wall of the operation section, and thus the operation for covering the operation section of the endoscope with the operation section cover becomes cumbersome.

Further, in the known endoscope system comprising the endoscope and disposable protection cover, when the insertion section of the endoscope is inserted into and removed from the insertion section cover, the insertion section inserting channel is inflated. That is to say, the insertion section inserting channel is communicated with an inflator via an inflating tube which is detachably secured to a nipple portion of the insertion section cover. Therefore, in such an endoscope system, it is necessary to provide the inflator separately from the endoscope apparatus including a video processing device, light source device and fluid control device. Moreover, it is necessary to provide a hanger from which the protection cover is hung when the endoscope is covered with the protection cover. Therefore, an effective space of the examination room is reduced by the provision of the inflator.

In case of using the inflator, usually the inflator is driven after the inflating tube is coupled with the nipple portion of the insertion section cover by actuating a power switch provided on the inflator. This is cumbersome for the user. Further, if the power switch is contaminated, there is a possibility that the new protection cover might be contaminated by the user.

Moreover, in case of inserting the insertion section of the endoscope into the insertion section inserting channel formed within the insertion section cover, the insertion section inserting channel is inflated by connecting the inflating tube to the nipple portion. In this case, if the nipple portion is formed at a position which is close to the opening of said insertion section inserting channel, the outlet of the nipple portion is closed by the insertion section when the insertion section is inserted into the insertion channel only slightly. Then, the air could not be efficiently supplied to the insertion channel and the insertion channel is not inflated sufficiently. In this manner, the insertion section of the endoscope could not be inserted into the insertion section inserting channel easily.

As explained above, in the endoscope system the inflator has to be provided for inflating the insertion section inserting channel. This increases the cost of the whole endoscope system, so that it is preferable to dispense the inflator.

SUMMARY OF THE INVENTION

The present invention has for its object to provide a novel and useful endoscope system including an endoscope having an insertion section to be inserted into a cavity under inspection, an operation section to which a proximal end of the insertion section is connected and a bending portion provided near a distal end of the insertion section, and a disposable protection cover for covering at least said insertion section of the endoscope and having at least one conduit channel formed therein, in which the distal end portion of the insertion section of the endoscope can be bent accurately and smoothly with a small force.

It is another object of the invention to provide a novel and useful endoscope system including an endoscope having an insertion section to be inserted into a cavity under inspection and an operation section to which a proximal end of the insertion section is connected and a disposable protection cover having an insertion section cover for covering said insertion section and an operation section cover for covering said operation section, in which the operation section of the endoscope can be easily covered with the operation section cover without being hindered by the shaft to which the angle knobs are secured.

It is another object of the invention to provide a novel and useful endoscope system including an endoscope having an insertion section to be inserted into a cavity under inspection and an operation section to which a proximal end of the insertion section is connected, a disposable protection cover having an insertion section cover for covering said insertion section of the endoscope and an insertion section inserting channel formed within said insertion section cover, and an inflator for inflating said insertion section inserting channel, in which a space for installing said inflator can be saved.

It is another object of the invention to provide a novel and useful endoscope system including an endoscope having an insertion section to be inserted into a cavity under inspection and an operation section to which a proximal end of the insertion section is connected, a disposable protection cover having an insertion section cover for covering said insertion section of the endoscope and an operation section cover for covering said operation section and an insertion section inserting channel formed within said insertion section cover, and an inflator for inflating said insertion section inserting channel, in which said insertion section inserting channel can be inflated without actuating a power switch of the inflator each time the insertion section is inserted into and removed from said inserting channel, so that the operation for inserting and removing said insertion section into and from said inserting channel can be simplified and the protection cover can be effectively prevented from being contaminated.

It is another object of the invention to provide a novel and useful endoscope system including an endoscope having an insertion section to be inserted into a cavity under inspection and an operation section to which a proximal end of the insertion section is connected, a disposable protection cover having an insertion section cover for covering said insertion section of the endoscope and an insertion section inserting channel formed within said insertion section cover, and an inflator for inflating said insertion section inserting channel, in which said insertion section inserting channel can be effectively inflated without being influenced by the inserted insertion section, so that the inserting operation can be performed easily.

It is still another object of the invention to provide a novel ad useful endoscope system including an endoscope having an insertion section to be inserted into a cavity under inspection and an operation section to which a proximal end of the insertion section is connected, a disposable protection cover having an insertion section cover for covering said insertion section of the endoscope and an insertion section inserting channel formed within said insertion section cover, and an inflator for inflating said insertion section inserting channel, in which said inflator can be dispensed with and the cost and size of the whole apparatus can be minimized.

According to a first aspect of the invention, an endoscope system including an endoscope having an insertion section to be inserted into a cavity under inspection, a bending portion which is provided in said insertion section near a distal end thereof and is bendable in at least two different directions and an operation section to which a proximal end of the insertion section is connected and a disposable protection cover having an insertion section cover for covering said insertion section of the endoscope and having formed therein an insertion section inserting channel into which said insertion section of the endoscope is insertable and at least one conduit channel, the improvement being characterized in that said insertion section and bending portion of the endoscope are formed to have a non-circular lateral cross section, a direction in which said non-circular cross section has a larger size is aligned with a direction in which said bending portion is bent by a maximum bending angle or a direction in which said non-circular cross section has a smaller size is aligned with a direction in which said bending portion is bent by a minimum bending angle.

In such an endoscope system according to the invention, the maximum bending direction is aligned with the larger size direction of the bending portion or the minimum bending direction is aligned with the smaller size direction of the bending portion, and therefore a large moment can be easily produced when the bending portion is bent in the maximum bending direction, because a distance between a fulcrum and a point of application at which an angle wire is secured can be increased. Therefore, the distal end of the insertion section can be directed into any desired direction by rotating the angle knob with substantially the same force.

According to a second aspect of the invention, an endoscope system including an endoscope having an insertion section to be inserted Into a cavity under inspection and an operation section to which a proximal end of the insertion section is connected and a disposable protection cover having an insertion section cover for covering said insertion section and an operation section cover for covering said operation section, the improvement being characterized in that said operation section comprises a housing, a shaft protruding from said housing at a top position remote from a position at which said insertion section is coupled with the operation section, and at least one angle knob secured to said shaft.

In this endoscope system according to the invention, the shaft and angle knob are provided at the top portion of the operation section of the endoscope, so that the operation section cover can be applied on the operation section of the endoscope easily without being hindered by the shaft and angle knob.

According to a third aspect of the present invention, an endoscope system including an endoscope having an insertion section to be inserted into a cavity under inspection and an operation section to which a proximal end of the insertion section is connected, a disposable protection cover having an insertion section cover for covering said insertion section of the endoscope and an insertion section inserting channel formed within said insertion section cover, and an inflator for inflating said insertion section inserting channel, the improvement being characterized in that the endoscope system further comprises a hanger for hanging at least said insertion section cover when the insertion section of the endoscope is inserted into and removed from the insertion section cover, and said inflator is provided within said hanger.

In the endoscope system according to the invention, the inflator is provided within the hanger for hanging the insertion section cover, and thus it is no more necessary to provide a space for arranging the inflator within an examination room.

In a preferable embodiment of the endoscope system according to the invention, said inflator installed within the hanger is constructed to be actuated automatically when the insertion section cover is set on the hanger. In another preferable embodiment of the endoscope system according to the invention, said inflator installed within the hanger is always kept operated. In these preferable embodiments, it is no more necessary to actuate a power switch of the inflator each time the insertion section is inflated and therefore the contamination can be avoided via the power switch.

According to a fourth aspect of the present invention, an endoscope system including an endoscope having an insertion section to be inserted into a cavity under inspection and an operation section to which a proximal end of the insertion section is connected, a disposable protection cover having an insertion section cover for covering said insertion section of the endoscope and an operation section cover for covering said operation section and an insertion section inserting channel formed within said insertion section cover, and an inflator for inflating said insertion section inserting channel, the improvement being characterized in that said inflator is kept always operated.

In such an endoscope system according to the invention, the inflator is always actuated, so that when an inflating tube is connected to the insertion section cover, the insertion section inserting channel is instantaneously inflated and it is not necessary to actuate a power switch of the inflator and the contamination via the power switch can be effectively avoided.

According to a fifth aspect of the present invention, an endoscope system including an endoscope having an insertion section to be inserted into a cavity under inspection and an operation section to which a proximal end of the insertion section is connected, a disposable protection cover having an insertion section cover for covering said insertion section of the endoscope and an insertion section inserting channel formed within said insertion section cover, and an inflator for inflating said insertion section inserting channel, the improvement being characterized in that said insertion section cover comprises a guide portion in which a guide hole is formed to be communicated with said insertion section inserting channel and a nipple portion to which an inflating tube is detachable secured is formed to be communicated with said guide hole, and a distance between an opening of said guide hole and said nipple portion is not less than an axial length of a distal end construction member provided at a distal end of said insertion section of the endoscope.

In the endoscope system according to the invention, the distance between the opening of the guide hole from which the insertion section of the endoscope is inserted into the insertion section inserting channel and the nipple portion is equal to or longer than the axial distance of the distal end contraction member made of rigid material of the insertion section, and thus a substantial length of the distal end portion of the insertion section has been inserted into the guide hole until the nipple portion is closed by the distal end portion. Therefore, the insertion section inserting channel can be sufficiently inflated and the insertion section can be easily inserted into the inserting channel. Further, the distal end portion of the insertion section can be positively held by the guide hole formed in the guide portion made of rigid material, so that the inserting operation can be improved.

According to a sixth aspect of the invention, an endoscope system including an endoscope having an insertion section to be inserted into a cavity under inspection and an operation section to which a proximal end of the insertion section is connected, a disposable protection cover having an insertion section cover for covering said insertion section of the endoscope and an insertion section inserting channel formed within said insertion section cover, and an inflator for inflating said insertion section inserting channel, in which said inflator is formed by an existing device such as light source device, air pump for supplying air from the distal end of the insertion section cover, stomach expanding device, heat probe unit, electro-surgical unit for diathermic cutter and ultrasonic endoscope device.

In such an endoscope system according to the invention, it is no more necessary to provide the separate inflator and thus the size and cost of the whole endoscope system can be reduced.

BRIEF DESCRIPTION OF THE DRAWINGS

FIG. 1 is a perspective view showing the whole construction of an embodiment of the endoscope system according to the invention;

FIG. 2 is a front view illustrating the construction of the operation section of the endoscope shown in FIG. 1;

FIG. 3 is a perspective view depicting the distal end of the insertion section of the endoscope;

FIG. 4 is a perspective view illustrating the construction of the distal end of the insertion section cover;

FIG. 6 is a lateral cross sectional view depicting the insertion section and insertion section cover;

FIG. 8 is a partially cross sectional view showing another embodiment of the operation section of the endoscope for use in the endoscope system according to the invention;

FIG. 9 is a cross sectional view showing the insertion section of the endoscope system according to the invention;

FIGS. 10A and 10B are side views showing the apparatus for supporting the insertion section cover according to the invention;

FIG. 12 is a perspective view showing another embodiment of the endoscope system according to the invention;

FIG. 13 is a schematic view illustrating the light source device shown in FIG. 12;

FIG. 14 is a graph showing the operation of the pump;

FIG. 15 is a cross sectional view showing the cover supporting apparatus shown in FIG. 12;

FIG. 16 is a cross sectional view illustrating another embodiment of the insertion section cover according to the invention;

FIG. 17 is a cross sectional view cut along a line A—A in FIG. 16;

FIG. 18 is a cross sectional view cut along a line B—B in FIG. 16

FIG. 19 is a cross sectional view cut along a line C—C in FIG. 16;

EXPLANATION OF THE PREFERRED EMBODIMENTS

Figure 5:
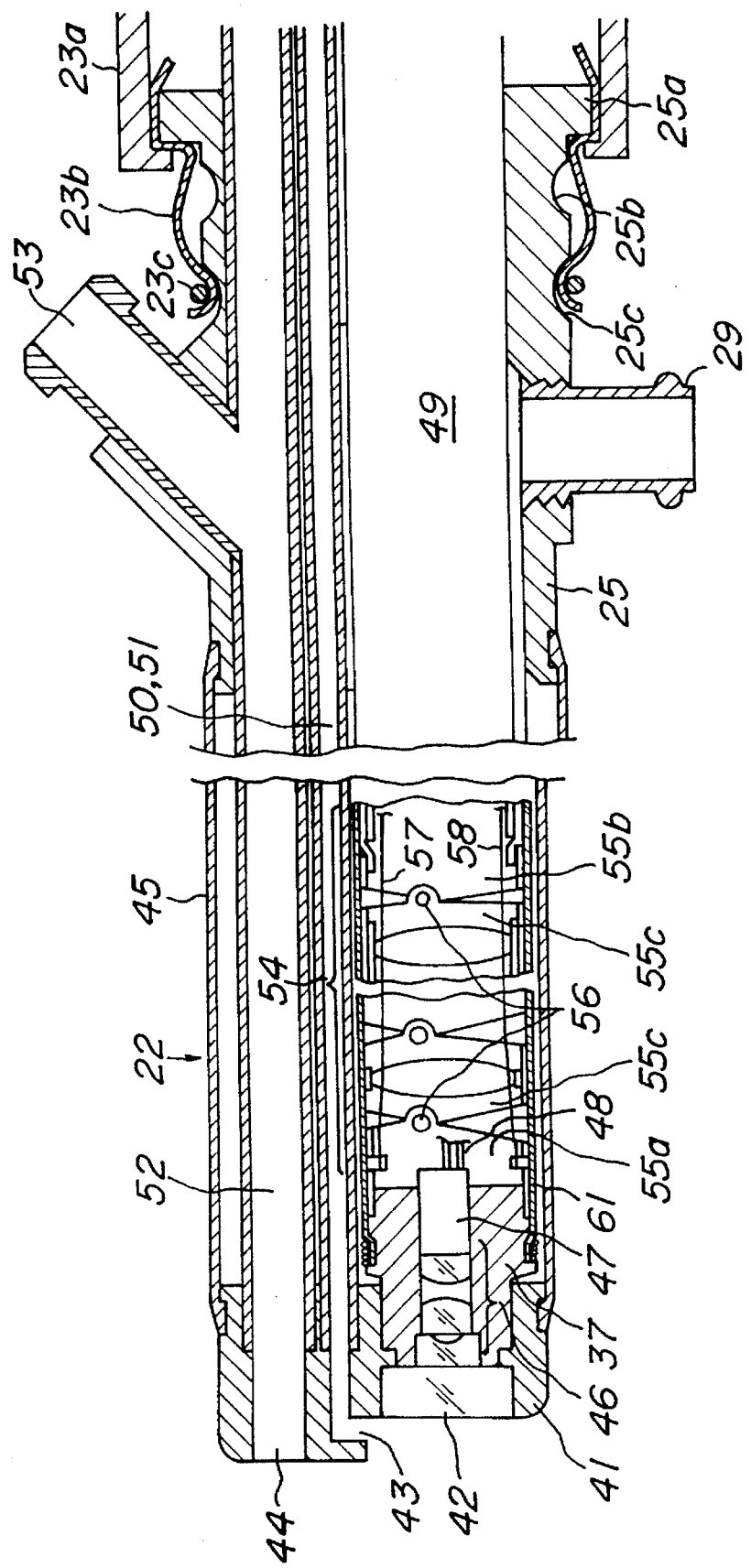
FIG. 5 is a longitudinal cross sectional view showing the endoscope system shown in FIG. 1.

FIG. 1 is a schematic view showing an embodiment of the endoscope system according to the invention including an endoscope apparatus and disposable protection cover. The endoscope apparatus comprises an endoscope 13 having an insertion section 11 and an operation section 12 with which a proximal end of the insertion section is coupled, and an external apparatus 14 coupled with the endoscope 13. The external apparatus 14 comprises a video processor 15 having a circuit for driving a solid state image sensor provided within a distal end of the insertion section 11 and a circuit for processing an image signal read out of the solid state image sensor, a monitor device 16 for displaying an image of an object under inspection by processing the image signal supplied from the video processor 15, a light source device 17 for emitting light for illuminating an inside of a cavity by means of a light guide optical fiber bundle extending within the insertion section 11, a fluid control device 18 having an air pump for supplying air and water, and an inflator 19 for inflating the disposable protection cover such that the insertion section 11 of the endoscope 13 can be easily inserted into and removed from the disposable protection cover as will be explained later in detail. These devices are installed in a box 20 having casters. The video processor 15 and light source device 17 are coupled with the operation section 12 of the endoscope 13 and the fluid control device 18 is coupled with conduit channels provided within the disposable protection cover by means of signal conductors, 1 light guide optical fiber bundle and tubes, respectively. These signal conductors, light guide optical fiber bundle and tubes are combined with each other into a universal cord 21. The universal cord 21 is detachably connected to the light source device 17 by means of a connector 21a and the signal conductors are connected to the video processor 15 by means of a cable 15a. The construction and operation of the above mentioned devices except for the inflator 19 are well known in the art, so that detailed explanation thereof is dispensed with.

The disposable protection cover of the present embodiment comprises an insertion section cover 22 for covering the insertion section 11 of the endoscope 13, an operation section cover 23 for covering the operation section 12 of the endoscope and a universal cord cover 24 for covering the universal cord 21. These disposable protection covers 22, 23 and 24 are formed separately from each other, and suitable coupling mechanisms are provided between junctions thereof in order to avoid a possible contamination through the junctions.

The protection covers 22, 23 and 24 may be made of various materials. For instance, flexible vinyl and rubber may be used as a soft material and rigid or semi-rigid plastics may be used as a hard material. It should be noted that the protection covers 22, 23 and 24 are not always necessary to be made of the same material, but may be made of different materials. For instance, the insertion section cover 22 may be made of flexible rubber, the operation section cover 23 may be made of rigid plastics and the universal cord cover 24 may be made of semi-rigid vinyl.

Prior to the actual examination, a set of protection covers is removed from a package and connecting portion 25 made of rigid or semi-rigid plastics and provided at a proximal end of the insertion section cover 22 is hung from a cover supporting member 27 of a cover supporting stand 26. In order to prevent the connecting portion 25 from being contaminated, the cover supporting member 27 may be covered with a disposable cover. As will be explained later, the connecting portion 25 of the insertion section cover 22 is utilized to couple the insertion section cover with the operation section cover 23.

A height of the cover supporting stand 26 has to be adjusted such that when the insertion section cover 22 is hung from the cover supporting member 27, the distal end of the disposable insertion section cover is not brought into contact with a floor. However, if a height of the cover supporting stand 26 is made too high, the inserting operation becomes difficult, so that the cover supporting stand could not be made so high. In such a case, the insertion section cover 22 has to be supported by an operator.

After the insertion section cover 22 has been hung from the cover supporting member 27, an end of an air supply tube 28 connected to the inflator 19 is coupled with a nipple portion 29 provided in the connecting portion 25 of the insertion section cover 22, and then the inflator 19 is driven to supply an air through the tube 28 into insertion section cover 22. In this manner, the insertion section cover 22 is inflated, so that the insertion section 11 of the endoscope 13 can be easily inserted into the insertion section cover 22. Then, the inflator 19 is de-energized and the tube 28 is decoupled from the nipple portion 29. This inflating operation is also performed upon removing the insertion section 11 form the insertion section cover 22. After the examination, the protection covers 22, 23 and 24 are discarded as medical dusts and the endoscope is cleaned and sterilized after all examinations for one day have been finished.

FIG. 2 shows the construction of the operation section 12 of the endoscope. To the operation section 12 are connected the insertion section 11 and universal cord 21. The operation section comprises a grip portion 31 and a main portion 32. The main portion 32 comprises angle knobs 33 for bending the distal end of the insertion section 11, air and water supply control switch 34, suction control switch 35 and function switch 36 for controlling the operation of a camera taking photographs of the object under inspection. In the present embodiment, the angle knobs 33 are detachably secured to the main portion 32 of the operation section 12. The angle knobs 33 may be of a disposable type which is contained in a package in which the disposable protection cover is installed or may be reused after sterilization.

FIG. 3 is a perspective view illustrating the construction of the insertion section 11 of the endoscope. In the present embodiment, a lateral cross section of a distal end construction member 37 is semicircular and in a front surface 38 of the member 37 there are arranged outlets of a pair of illuminating optical systems, i.e. optical fiber bundles 39 and an aperture 40 of an observing optical system provided between the illuminating optical systems.

FIG. 4 is a perspective view depicting the construction of a distal end of the insertion section cover 22 and FIGS. 5 and 6 are longitudinal and lateral cross sectional views showing the insertion section cover 22 into which the insertion section 11 of the endoscope is inserted. In a front surface of a distal end construction member 41 of the insertion section cover 22, there are provided a semicircular observation window 42 made of transparent material, a nozzle 43 for ejecting air and water toward the window 42, and an outlet opening 44 of a forceps channel 52. By ejecting the air and water from the nozzle 43, the outer surface of the observation window 42 can be cleaned.

To the distal end construction member 41 of the insertion section cover 22, is connected one end of an insertion section cover tube 45 which isolates a main portion of the insertion section 11 from the external. This cover tube 45 is made of a flexible material. In the present embodiment, the cover tube 45 is made of flexible rubber. The other end of the cover tube 45 is connected to the connecting portion 25 of the insertion section cover 22.

As illustrated in FIG. 5, within the distal end construction member 37 of the insertion section 11 which is faced with the observation window 42 of the distal end construction member 41 of the insertion section cover 22, there are arranged observing lens system 46 for forming an image of an object under inspection and a solid state image sensor 47 for picking-up the image of an object under inspection. The solid state image sensor 47 is electrically connected to the video processor 15 (FIG. 1) by means of signal conductors 48 extending through the insertion section 11 and universal cord 21.

Within the insertion section cover 22, there are formed an endoscope inserting channel or insertion section inserting channel 49 into which the insertion section 11 is inserted, air supply conduit 50 communicated with the air and water ejecting nozzle 43, water supply conduit 51 also communicated with the nozzle 43, and forceps channel 52. These channels and conduits are arranged in parallel with each other. The forceps channel 52 is communicated with a forceps inlet opening 53 provided in the connecting portion 25 and is also communicated with the fluid control device 18 by means of a conduit tube provided within the universal cord 21. Therefore, the forceps channel 52 is used as a suction tube and is sometimes called a suction channel. Further, the conduits 50 and 51 are also called conduit channels in the present specification.

In order to bend the distal end of the insertion section 11 by operating the angle knobs 33 such that an optical axis of the observing optical system 46 is moved up and down as well as right and left, there is provided a bending portion 54 adjacent to the distal end construction member 37 of the insertion section 11 of the endoscope. The bending portion 54 comprises a series of nodal rings 55 which are coupled with each other by means of journal pins 56 and a remotest ring is connected to the distal end construction member 37 of the insertion section 11. Two pairs of wires 57, 58 and 59, 60 are secured to the front end ring 55 at diametrically opposing points. These wires 57 to 60 are extended within the insertion section 11 and are wound around a pair of pulleys provided in the operation section 12. In FIG. 5, only one pair of wires 57 and 58 are shown, but two pairs of wires 57 to 60 are illustrated in FIG. 6. A series of nodal rings 55 is covered with a flexible rubber tube 61 in a liquid tight manner. By operating the angle knobs 33, the pulleys may be rotated and thus the wires 57 to 60 may be moved such that the bending portion 54 is moved in the up and down directions as well as in the left and right directions and the distal end of the insertion section 11 is directed into a desired direction. This construction is well known in the art, so that its detailed explanation may be dispensed with. At a proximal end of the connecting portion 25 there are formed a ring shaped recess 25a for connecting the operation section cover 23 and a ring shaped recesses 25b for engaging the connecting portion with the supporting member 27 on the supporting stand 26.

In the present embodiment, the insertion section 11 of the endoscope has a substantially semicircular cross section and the air and water supply conduit channels 50 and 51 and the forceps channel 52 are arranged within a remaining space having a substantially semicircular cross section as shown in FIG. 6. In this case, the insertion section 11 and the conduit channels 50 to 52 are aligned in the up and down directions, so that the distal end portion can be easily bent in these directions. It should be noted that according to the invention, these conduit channels may be formed in the form of a multi-lumen tube.

Figure 7A:
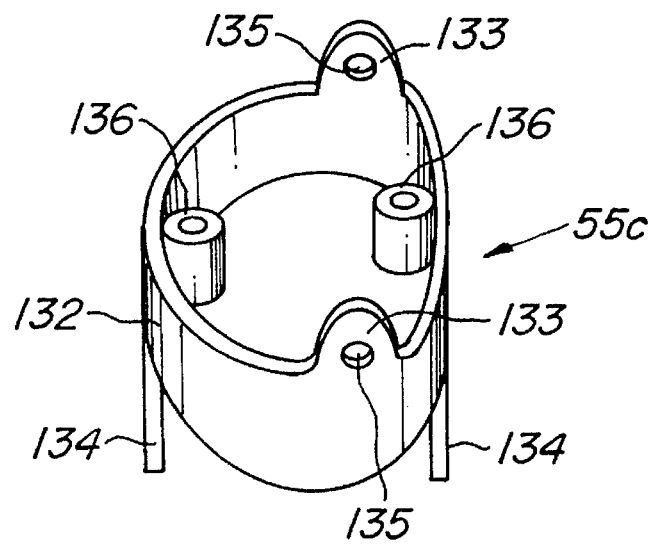
FIGS. 7A, 7B and 7C are perspective views representing three different types of the intermediate nodal rings.

As shown in FIG. 5, the bending portion 54 comprises remotest nodal ring 55a, nearest nodal ring 55b and intermediate nodal rings 55c. There are prepared several types of the intermediate nodal rings 55c. FIG. 7A illustrates the intermediate nodal ring 55c used in the present embodiment. This nodal ring 55c comprises a substantially semicircular cylindrical body 132 having lugs 133 formed at both ends of a major axis of the semicircular cylindrical body and lugs 134 formed at both ends of a minor axis. In these lugs 133 and 134 there are formed holes 135 through which journal pins 56 shown in FIG. 5 are inserted. On an inner wall of the cylindrical body 132 there are formed wire receptacles 136 at both ends of the minor axis through which the wires 57 and 58 are passed.

Figure 7B:
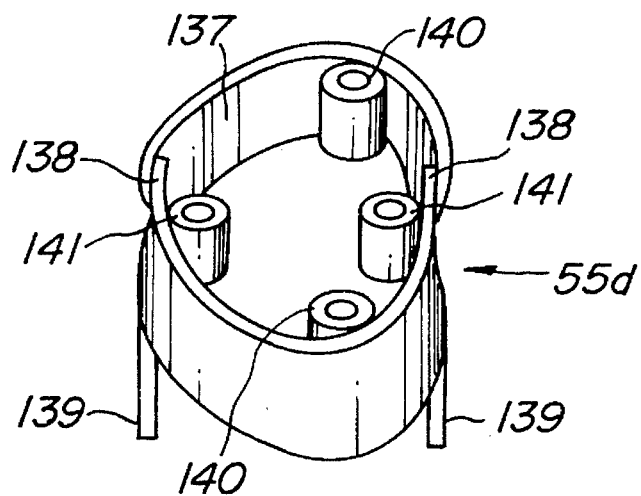

FIG. 7B shows another embodiment of the intermediate nodal ring 55d. The nodal ring 55d comprises a semicircular cylindrical body 137 having lugs 139 and 141 at both ends of the minor axis of the semicircular cylindrical body 137. In these lugs 139 and 141 have formed therein holes for inserting the journal pins 56. In an inner wall of the cylindrical body 137 there are formed wire receptacles 140 at both ends of the minor axis for guiding the wires 57 and 58 as well as wire receptacles 141 at both ends of the major axis for guiding the wires 59 and 60.

Figure 7C:
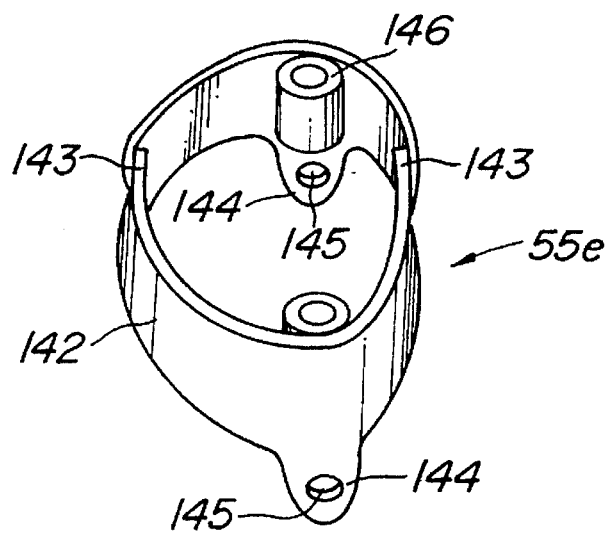

In an embodiment of the intermediate nodal ring 55e shown in FIG. 7C, in an upper edge of a substantially semicircular cylindrical body 142 there are formed lugs 143 having holed formed therein at both ends of the minor axis and in a lower edge of this body there are formed lugs 144 at both ends of the major axis and holes 145 are formed in these lugs. In the inner wall of the semicircular cylindrical body 142, there are formed wire receptacles 146 at both ends of the major axis.

FIG. 8 is a partial cross sectional view showing an embodiment of a driving mechanism provided in the operation section 12 of the endoscope for driving the wires 57 to 60 by operating the angle knobs 33a and 33b. It should be noted that in the embodiment shown in FIGS. 1 to 6, the angle knobs 33 are provided on the side wall of the operation section 12, but in the present embodiment, the angle knobs 33a and 33b are provided on the top wall of the operation section which is remote from the bottom wall from which the insertion section 11 having the bending portion 54 is extended. Therefore, in the present embodiment, the operation section cover can be easily applied on the operation section 12 without being hindered by the angle knobs 33a and 33b which are detachably secured to shafts 150 and 153, respectively extending coaxially from a top wall of a housing 129 of the operation section 11. Within the housing 129, there are arranged first and second pulleys 148 and 151, and the wires 57 and 58 are round around the first pulley 148 and the wires 59 and 60 are wound around the second pulley 151. The first pulley 148 is coupled with the first shaft 150 by means of a first bevel gear chain 149 and the second pulley 151 are coupled with the second shaft 153 by means of second bevel gear chain 152. Top portions of the first and second shafts 150 and 153 are formed to have rectangular cross sections and in the angle knobs 33a and 33b there are formed corresponding rectangular holes. Therefore, by inserting the top portions of the shafts 150 and 153 into these holes, it is possible to detachably secured to the angle knobs to the shafts. By rotating the angle knob 33a, the bending portion 54 of the insertion section 11 can be bent in the right and left directions and by operating the angle knob 33b the bending portion can be bent in the up and down directions. In this manner, the distal end of the insertion section 11 can be directed at will in any desired direction.

FIG. 9 is a cross sectional view of the bending portion 54 of the insertion section 11. In FIG. 9, a line B—B denotes an axis about which the bending portion is bent in the up and down directions and a line C—C represents an axis about which the bending portion is bent in the right and left directions. Now it is assumed that distances between these axes B—B and C—C are denoted as l1 to l4 as shown in FIG. 9. According to the present embodiment, these distances are set to satisfy the following equation.

$$l1=l3>l4>l2.$$

The inventors have found that it is preferable to set l1 to 2.5–7.5 mm, l1 is larger than l4 by 1.2 to 2.5 times and l1 is larger than l2 by 2.8 to 5 times. Therefore, for instance l1=l3=5 mm, l4=4 mm and l2=2 mm.

When the wire 59 is pulled by operating the angle knob 33b, the bending portion 54 is bent in a direction A—A in FIG. 6, i.e. a direction parallel to the direction of the main axis of the semicircular cross section. In the present embodiment, this direction is set to the up direction in which the bending portions 54 to be bent by a maximum bending angle. In this case, the bending angle is different in accordance with organs to be examined, and generally the bending angle is 160 to 240 degrees. Similarly, when the wire 60 is pulled by operating the angle knob 33b in the opposite direction, the bending portion can be bent in the down direction by a bending angle which is determined by the distance l3.

When the wire 57 is pulled by operating the angle knob 33a, the bending portion 54 is bent in a direction perpendicular to the direction A—A, i.e. in the right direction. Since the distance l2 is smallest, the bending angle in this right direction is smallest and is generally 80 to 170 degrees. Similarly when the wire 58 is pulled, the bending portion is bent in the left direction.

As explained above, according to the present invention, the bending angles can be determined in relation to the distances l1 to l4 which are then determined by the mutual arrangement of the insertion section 11 of the endoscope and conduit channels 50 to 52 within the insertion section cover 22. In the upper type endoscope, the bending angles in the up, down, left and right directions are set to 210, 90, 100 and 100 degrees, respectively, and in a lower endoscope these bending angles are set to 180, 180, 160 and 160 degrees, respectively. Further, the bending angles in the up, down, left and right directions may be set to 100, 100, 100 and 90 degrees.

In the present embodiment, the bending portion has to be bent in the upward direction by the largest bending angle, and the distance l1 between the wire 59 and the axis C—C is longest, so that a largest moment can be produced for bending the bending portion in the upward direction. In the right direction, the moment is smallest owing to the reason that the distance l2 is shortest, but the bending angle in this right direction is smallest. Therefore, the distal end of the insertion section can be bent in any desired direction smoothly. In this manner, the bending portion of the insertion section is constructed such that the largest moment is produced in the direction in which the bending portion has to be bent by the largest bending angle, or the bending portion of the insertion section is constructed such that the smallest moment is produced in the direction in which the bending portion has to be bent by the smallest bending angle.

Figure 11:
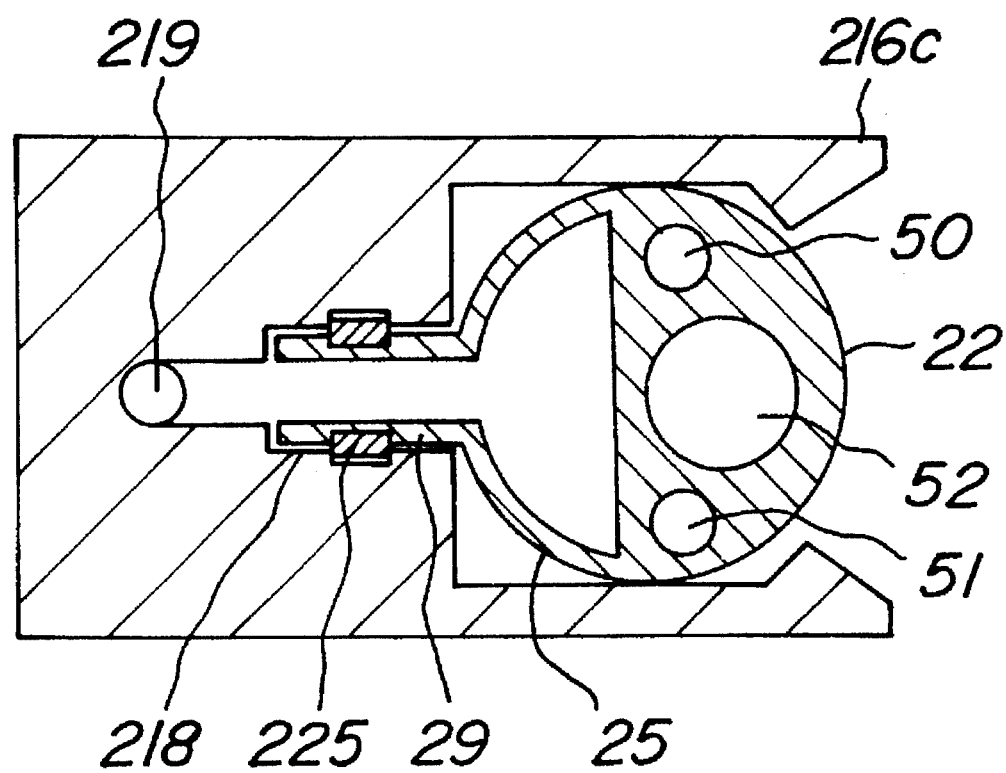
FIG. 11 is a cross sectional view cut along a line D—D in FIG. 10B.

FIGS. 10A, 10B and 11 show an embodiment of the cover supporting apparatus according to the invention, in which the inflator is installed within a stand of the cover supporting apparatus. FIG. 10A is a side view illustrating the endoscope supported on an endoscope supporting apparatus 215 and FIG. 10B is a side view depicting the insertion section cover 22 with the connecting portion 25 supported on the cover supporting apparatus 216 according to the invention. The cover supporting apparatus 216 comprises a base portion 216a in which an inflating pump 217 is arranged, a stand 216a secured to the base portion 216a and a hanger portion 216c secured to a top of the stand 216b. As explained above, the connecting portion 25 of the insertion section cover 22 is supported by the hanger portion 216c. Within the stand 216b there is arranged an inflating tube 219 whose one end is connected to the pump 217 and whose other end is detachably coupled with the nipple portion 29 formed on the connecting portion 25. Tubes 221, 222 and 223 are connected to the conduit channels 50, 51 and 52, respectively formed within the insertion section cover 22. On an outer of the base portion 216a there is arranged a power switch 220 for actuating the inflating pump 217.

FIG. 11 is a cross sectional view cut along a line D—D in FIG. 10B. As shown in FIG. 11, in the hanger portion 216c there is formed a receptacle 218 into which the nipple portion 29 of the connecting portion 25 is inserted when the insertion section cover 22 is hung on the hanger portion 216c. That is to say, the nipple portion 29 is clamped in a click fashion within the receptacle 218 by means of a C-ring 225 made of resilient material.

When the insertion section cover 22 is hung on the hanging portion 216b, the nipple portion 29 of the insertion section cover is inserted into the receptacle 218 and is communicated with the inflating tube 219. Then, the power switch 220 is actuated to operate the inflating pump 217 provided within the base portion 216a of the cover supporting apparatus 216, so that the insertion section inserting channel formed within the insertion section cover 22 is inflated. In this manner, the insertion section 11 can be easily inserted into the inflated insertion section inserting channel. According to the present embodiment, the inflating pump 217 is arranged within the cover supporting apparatus 216, so that it is no more necessary to prepare the special external apparatus 14 including the inflator 19 as shown in FIG. 1.

According to the present invention, the power switch 220 provided on the cover supporting apparatus 216 may be driven in conjunction with a main switch 225 provided on the external apparatus 14 as depicted in FIG. 1. In this case, the video processor 15, light source device 17 and fluid control device 18 may be simultaneously made ON.

Furthermore, the power switch 220 of the inflating pump 217 may be dispensed with by actuating the inflating pump 217 in response to the actuation of any one of switches of devices provided in the external apparatus 14. Further the power switch 220 may be deleted by connecting the inflating pump 217 to a plug via a cord. Then, when the plug is inserted into a socket, the inflating pump 217 is actuated, so that it is no more necessary to operate the switch 220 every time the inflating operation is carried out and thus the protection cover can be effectively prevented from being contaminated via the switch. Moreover, the power switch 220 may be formed as a foot switch. Also in this case, the protection cover can be prevented from being contaminated.

As explained above, in case of inserting the insertion section 11 of the endoscope into the insertion section channel 49 formed within the insertion section cover 22, the insertion section inserting channel is inflated. According to the present invention, the inserting operation can be performed easily and effectively. In the embodiment shown in FIGS. 1 to 5, the external apparatus 14 includes the inflating device 19 for inflating the insertion section inserting channel 49 formed within the insertion section cover 22, and in the embodiment illustrated in FIG. 10B, the inflating pump 217 is arranged within the cover supporting apparatus 216. According to the invention, the inflating pump may be formed by an air pump installed in one of various existing devices such as the light source device, air pump for supplying air from the distal end of the insertion section cover, stomach expanding device, heat probe unit, electrosurgical unit for diathermic cutter and ultrasonic endoscope device.

FIG. 12 is a perspective view showing another embodiment of the endoscope system according to the invention. Portions similar to those illustrated in FIG. 1 are denoted by the same reference numerals used in FIG. 1 and their detailed explanation is dispensed with. In the present embodiment, the inflating pump is formed by an air pump provided in an light source device 302 for supplying the air through the air supply conduit tube. That is to say, as illustrated in FIG. 13, the light source device 302 comprises a lamp 318 emitting light which is transmitted to the distal end of the insertion section 11 via the light guide optical fiber bundle 39 and an air pump 321 for supplying the air through a valve 324. To a conduit between the pump 321 and the valve 324 is connected a branch 323 which is coupled with a nipple portion 322. An inflating tube 315 is coupled with the nipple portion 322.

When the pump 321 is used as the inflating pump, the valve 324 is closed so that the air is supplied to the inflating tube 315. In this case, the pump 321 is operated in a pulsatory manner as shown in FIG. 14 so that the insertion section 11 of the endoscope can be inserted into the inflated insertion section inserting channel much more easily. When the pump 321 is used as the pump for supplying the air to the air supply conduit tube, the valve 324 is opened. In the present embodiment, it is no more necessary to provide the inflating pump separately from the air pump 321 provided in the light source device 302. In the present embodiment, as shown in FIG. 12, a video recording device 305 is provided in the box 20 for recording the video signal supplied from the video processor 15.

As shown in FIG. 12, in the present embodiment, a cover supporting apparatus 314 comprises first and second hanger portions 316 and 317. The first hanger portion 316 belongs to the clean area and a new insertion section cover is hung when the insertion section of the endoscope is inserted into the insertion section cover and the second hanger portion 317 belongs to the non-clear or contaminated area and a used insertion section cover is hung when the insertion section of the endoscope is removed from the insertion section cover.

FIG. 15 is a cross sectional view illustrating a detailed construction of the cover supporting apparatus 314 according to the invention. The construction of the first and second hanging portion 316 and 317 are same and comprise arm portions 324a, 324b and 325a, 325b and nipple portions 326 and 367 with which the nipple portion 29 of insertion section cover 22 is detachably coupled. Within the nipple portions 326 and 327, there are provided receptacles 328 and 329, respectively which are resiliently urged against O-rings 322 and 323 by means of coiled springs 330 and 331, so that the nipple portions 326 and 327 are closed in an air tight manner when the nipple portion 29 of the insertion section cover is not clamped with these nipple portions 326 and 327. The nipple portions 326 and 327 are communicated with the inflating tube 315 by means of tubes 334 and 335 and T type coupler 336.

FIG. 16 is a longitudinal cross sectional view showing another embodiment of the endoscope system according to the invention, in which the insertion section of the endoscope has been inserted into the insertion section inserting channel formed within the insertion section cover insertion section cover 22. Portions of the present embodiment similar to those of the previous embodiments are denoted by the same reference numerals and their explanation is dispensed with. Also in the present embodiment, the insertion section cover 22 comprises the connecting portion 25 in which the faceps inlet 53 and the nipple portion 29 are formed. Lateral cross sectional views cut along lines A—A, B—B and C—C are shown in FIGS. 17, 18 and 19, respectively. As illustrated in FIGS. 17 to 19, in the present embodiment, the conduit channels 50 to 52 are formed within a multi-lumen tube 352 having a substantially semicircular cross section. In FIGS. 17 to 19, the insertion section 11 is represented as a solid body for the sake of simplicity and is inserted into the insertion section inserting channel 49 having a substantially semicircular cross section. As shown in FIG. 18, the insertion section inserting channel 49 has a larger space at a position in which the nipple portion 29 is formed than that of the remaining portion, so that a wider space is formed between the outer wall of the insertion section 11 of the endoscope and the inner wall of the insertion section inserting channel 49. Further, at a portion where the above mentioned space is communicated with an inner space 354 of the nipple portion 29 there is formed a wider space 355. In this manner, the nipple portion 29 can be effectively prevented from being clogged by the insertion section 11, so that the insertion section inserting channel 49 can be effectively inflated. Furthermore, as illustrated in FIG. 19, in an inner wall of the cover tube 45 there are formed a plurality of grooves 358 through which the air can be effectively introduced into the inserting channel 49.

In the present embodiment, a distance W of a portion of the connecting portion 25 from the nipple portion 29 and an inlet opening 346 of the insertion section inserting channel 49 is set to be longer than a distance M of the rigid distal end portion of the insertion section 11. Therefore, said portion of the connecting portion 25 can serve as a guide for the distal end portion of the insertion section when the insertion section is inserted into the inserting channel 49, so that the inserting operation can be performed easily. Moreover, the distance W of said portion of the connecting portion 25 is long, and thus the nipple portion 29 is not clogged by the rigid distal end portion of the insertion section and the inserting channel 49 can be effectively inflated without being hindered by the rigid distal end portion of the insertion section.

The present invention is not limited to the embodiments explained above, but many modifications and alternations may be conceived by those skilled in the art within the scope of the invention. For instance, the cover supporting apparatus may comprises a sensor for detecting that the insertion section cover 22 is hung on the hanger portion of the cover supporting apparatus and the inflating pump may be actuated in response to an output signal of said sensor. In this case, the power switch for the inflating pump may be dispensed with.

Figure 20A:
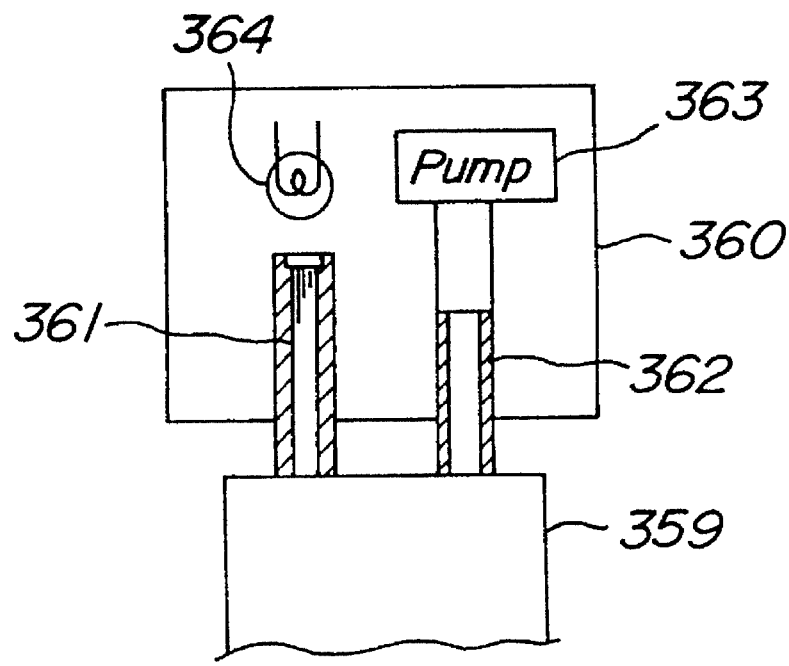
FIGS. 20A and 20B are schematic view showing the light source device for use in the endoscope system according to the invention.
Figure 20B:
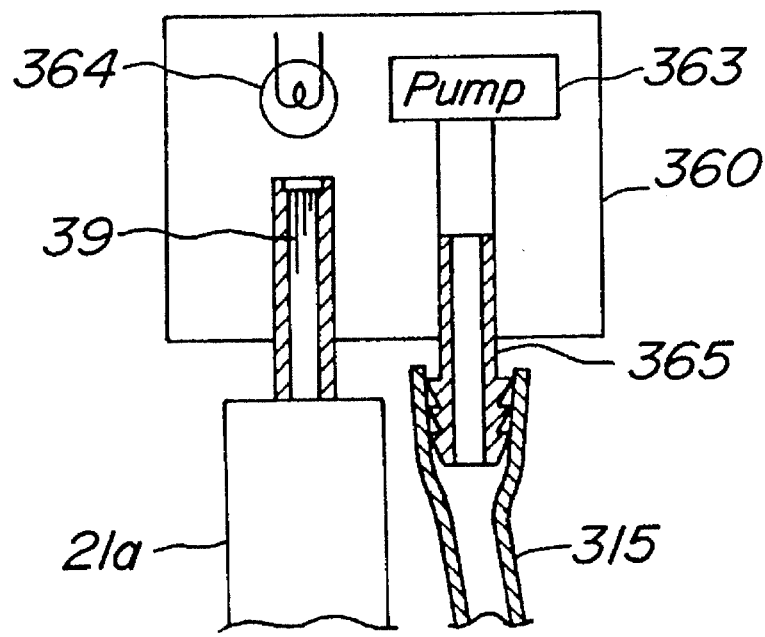

Further, in the embodiment shown in FIGS. 12 and 13, the air supply pump 321 installed in the light source device 17 is used to inflate the insertion section inserting channel 49 of the insertion section cover 22. It is also possible to utilize a known light source device for the ordinary without-cover endoscope. When a light source device 360 is used for the ordinary without-cover endoscope as shown in FIG. 20A, a connector 359 connected at an end of a universal cord and including a light guide optical fiber bundle 361 and a conduit tube 362 communicate with an air supply conduit channel formed within an insertion section of the endoscope is connected to the light source device 360 such that the light guide optical fiber bundle 361 is faced to a lamp 364 and the conduit tube 362 is coupled with a pump 363. When such a light source device 360 is used in the endoscope system according to the invention, the connector 21a is connected to the light source device 360 such that the light guide optical fiber bundle 39 is faced with the lamp 364, and the inflating tube 315 is detachably connected to a nipple portion 365 communicated with the pump 363. After the insertion section has been inserted into the insertion section cover, the inflating tube 315 is removed from the nipple portion 365 and the conduit tube communicated with the air supply conduit channel 50 is connected to the nipple portion 365.

Figure 21:
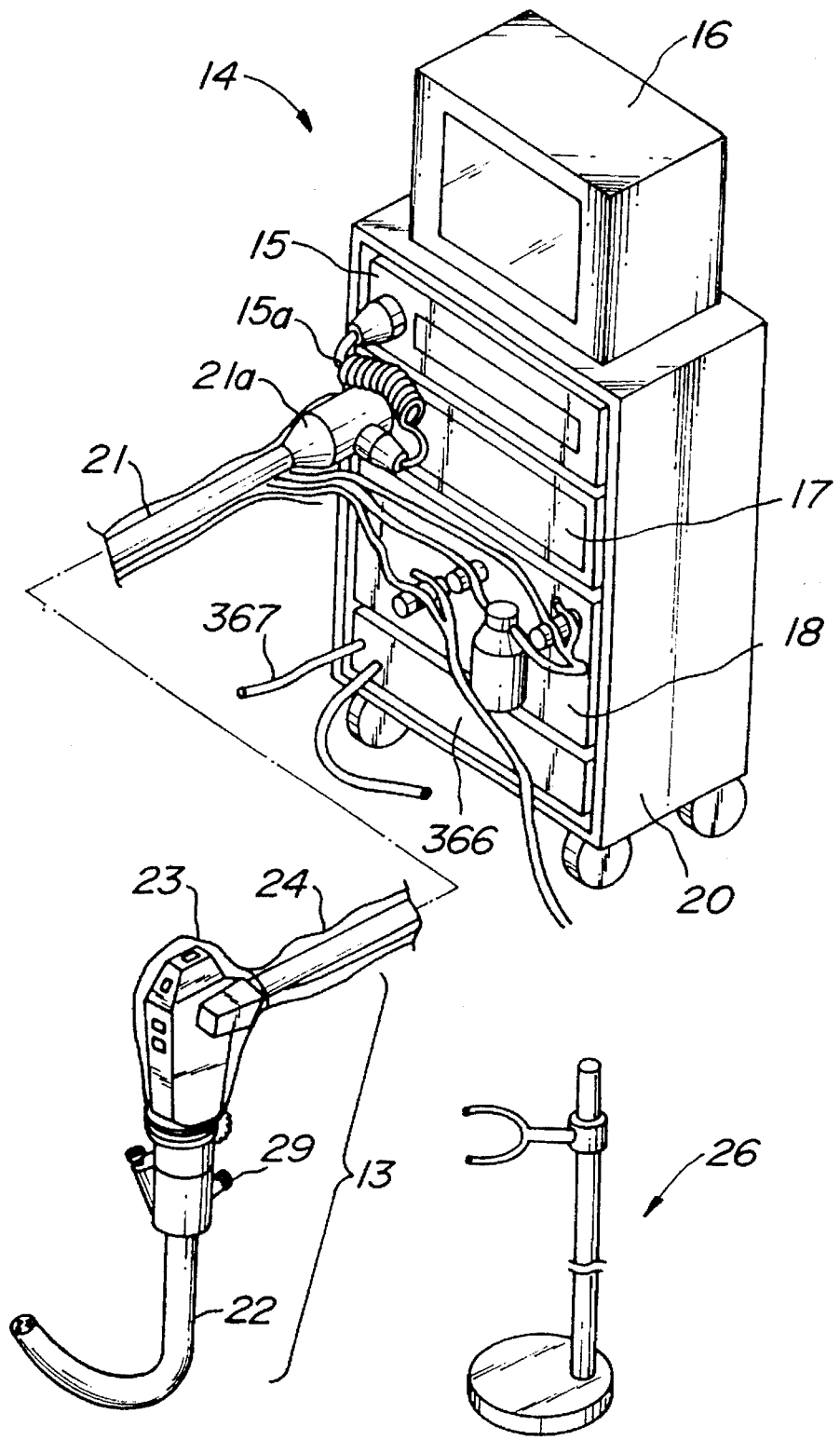
FIG. 21 is a perspective view showing another embodiment of the endoscope system according to the invention.

Further in the above embodiment, the insertion section inserting channel is inflated by utilizing the air supply pump installed within the light source device, but according to the invention, any other pump provided in other devices such as the heat probe unit, stomach expanding device, electro-surgical unit for diathermic cutter and ultrasonic endoscope device. FIG. 21 is a perspective view showing another embodiment of the endoscope system according to the invention, in which the insertion section inserting channel is inflated by utilizing a pump provided in the stomach expanding device. A stomach expanding device 366 is arranged within the box 20 of the external apparatus 14 and includes an air pump not shown. An inflating tube 367 communicated with said air pump is extended from the stomach expanding device 366. By connecting the inflating tube 367 to the nipple portion 29 of the insertion section cover 22, it is possible to inflate the insertion section inserting channel formed within the insertion section cover.

What is claimed is:

1. An endoscope system including an endoscope having an insertion section to be inserted into a cavity under inspection and an operation section to which a proximal end of the insertion section is connected and a protection cover having an insertion section cover for covering said insertion section and an operation section cover for covering said operation section, wherein said operation section comprises a housing having a first longitudinal end to which said insertion section is coupled, a shaft protruding from a second longitudinal end of said housing which is opposite said first longitudinal end, and at least angle knob secured to said shaft near said second longitudinal end.

* * * * *